United States Patent
Dekker

(10) Patent No.: US 6,702,752 B2
(45) Date of Patent: Mar. 9, 2004

(54) MONITORING RESPIRATION BASED ON PLETHYSMOGRAPHIC HEART RATE SIGNAL

(75) Inventor: Andreas Lubbertus Aloysius Johannes Dekker, Maastricht (NL)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/081,719

(22) Filed: Feb. 22, 2002

(65) Prior Publication Data

US 2003/0163054 A1 Aug. 28, 2003

(51) Int. Cl.⁷ .................................. A61B 5/02
(52) U.S. Cl. ................. 600/484; 600/483; 600/500; 600/479
(58) Field of Search ................ 600/484, 483, 600/481, 500, 501, 502, 504, 507, 508, 476, 479, 480, 473, 475, 529

(56) References Cited

U.S. PATENT DOCUMENTS

| | | |
|---|---|---|
| 3,704,706 A | 12/1972 | Herczfeld et al. |
| 4,306,567 A | 12/1981 | Krasner |
| 4,379,460 A | 4/1983 | Judell |
| 4,404,974 A | 9/1983 | Titus |
| 4,510,944 A | 4/1985 | Porges |
| 4,765,340 A | 8/1988 | Sakai et al. |
| 4,777,960 A | 10/1988 | Berger et al. |
| 4,781,201 A | 11/1988 | Wright et al. |
| 4,813,427 A | 3/1989 | Schlaefke et al. |
| 4,858,638 A | 8/1989 | Cseri ........................... 137/115 |
| 4,860,759 A | 8/1989 | Kahn et al. |
| 4,863,265 A | 9/1989 | Flower et al. |
| 4,869,254 A | 9/1989 | Stone et al. |
| 4,884,578 A | 12/1989 | Morgenstern |
| 4,899,760 A | 2/1990 | Jaeb et al. |
| 4,930,517 A | 6/1990 | Cohen et al. |
| 4,958,638 A | 9/1990 | Sharpe et al. |
| 4,960,129 A | 10/1990 | DePaola et al. |
| 4,972,842 A | 11/1990 | Korten et al. |
| 5,033,472 A | 7/1991 | Sato et al. |
| 5,078,136 A | 1/1992 | Stone et al. |
| 5,111,817 A | 5/1992 | Clark et al. |
| 5,170,794 A | 12/1992 | Reiche |
| 5,273,036 A | 12/1993 | Kronberg et al. |
| 5,368,224 A | 11/1994 | Richardson et al. |
| 5,385,144 A | 1/1995 | Yamanishi et al. |
| 5,396,893 A | 3/1995 | Oberg et al. |
| 5,423,322 A | 6/1995 | Clark et al. |
| 5,431,159 A | 7/1995 | Baker et al. |
| 5,482,036 A | 1/1996 | Diab et al. |
| 5,490,505 A | 2/1996 | Diab et al. |
| 5,511,553 A | 4/1996 | Segalowitz |
| 5,553,615 A | 9/1996 | Carim et al. |

(List continued on next page.)

OTHER PUBLICATIONS

Spectral Analysis: Review "Heart Rate Variability", Lukas Spieker, hemodynamics.ucdavis.edu, Unknown Publication Date.

Primary Examiner—Max F. Hindenburg
Assistant Examiner—Navin Natnithithadha
(74) Attorney, Agent, or Firm—Marsh Fischmann & Breyfogle LLP

(57) ABSTRACT

A pleth signal is analyzed to identify a heart rate variability parameter associated with respiration rate. In one embodiment, an associated process involves obtaining a photoplethysmograpic signal, processing the pleth signal to obtain heart rate samples, monitoring the heart rate sample to identify a heart rate variability associated with respiration, and determining a respiration rate based on the heart rate variability. The photoplethysmographic signal may be based on one or more channel signals of a conventional pulse oximeter. The invention thus allows for noninvasive monitoring of respiration rate and expands the functionality of pulse oximeters.

38 Claims, 8 Drawing Sheets

U.S. PATENT DOCUMENTS

| | | |
|---|---|---|
| 5,555,882 A | 9/1996 | Richardson et al. |
| 5,575,284 A | 11/1996 | Athan et al. |
| 5,623,933 A | 4/1997 | Amano et al. |
| 5,755,229 A | 5/1998 | Amano et al. |
| 5,766,127 A | 6/1998 | Pologe et al. |
| 5,776,071 A | 7/1998 | Inukai et al. |
| 5,830,137 A | 11/1998 | Scharf |
| 5,842,979 A | 12/1998 | Jarman ........................ 600/322 |
| 5,853,364 A | 12/1998 | Baker, Jr. et al. |
| 5,862,805 A | 1/1999 | Nitzan |
| 5,865,167 A | 2/1999 | Godik |
| 5,865,756 A | 2/1999 | Peel, III |
| 5,885,213 A | 3/1999 | Richardson et al. |
| 5,902,235 A | 5/1999 | Lewis et al. ................. 600/323 |
| 5,919,134 A | 7/1999 | Diab ........................... 600/323 |
| 5,931,779 A | 8/1999 | Arakaki et al. ............. 600/310 |
| 5,934,277 A | 8/1999 | Mortz |
| 5,954,644 A | 9/1999 | Dettling et al. .............. 600/322 |
| 5,971,930 A | 10/1999 | Elghazzawi .................. 600/483 |
| 5,980,463 A | 11/1999 | Brockway et al. |
| 5,993,893 A | 11/1999 | Kikuchi ........................ 427/8 |
| 5,997,482 A | 12/1999 | Vaschillo et al. ........... 600/484 |
| 6,011,985 A | 1/2000 | Athan et al. ................. 600/322 |
| 6,027,455 A | 2/2000 | Inukai et al. ................ 600/490 |
| 6,028,311 A | 2/2000 | Sodickson et al. .......... 250/343 |
| 6,064,910 A | 5/2000 | Andersson et al. ........... 607/20 |
| 6,067,462 A | 5/2000 | Diab et al. ................... 600/310 |
| 6,081,742 A * | 6/2000 | Amano et al. .............. 600/513 |
| 6,099,481 A | 8/2000 | Daniels et al. .............. 600/538 |
| 6,129,675 A | 10/2000 | Jay ............................ 600/485 |
| 6,155,992 A | 12/2000 | Henning et al. ............. 600/583 |
| 6,480,733 B1 | 11/2002 | Turcott ........................ 600/516 |

* cited by examiner

MONITORING RESPIRATION BASED ON PLETHYSMOGRAPHIC HEART RATE SIGNAL

FIELD OF THE INVENTION

The present invention relates, in general, to the noninvasive monitoring of respiration rate based on optical (visible and/or non-visible spectrum) signals and, in particular, to monitoring respiration based on the processing of received optical signals to identify heart rate variability associated with respiration. The invention can be readily implemented in connection with pulse oximetry instruments so as to expand the utility of such instruments.

BACKGROUND OF THE INVENTION

Photoplethysmography relates to the use of optical signals transmitted through or reflected by a patient's blood, e.g., arterial blood or perfused tissue, for monitoring a physiological parameter of a patient. Such monitoring is possible because the optical signal is modulated by interaction with the patient's blood. That is, interaction with the patient's blood generally involving a wavelength and/or time dependent attenuation due to absorption, reflection and/or diffusion, imparts characteristics to the transmitted signal that can be analyzed to yield information regarding the physiological parameter of interest. Such monitoring of patients is highly desirable because it is noninvasive, typically yields substantially instantaneous and accurate results, and utilizes minimal medical resources, thereby proving to be cost effective.

A common type of photoplethysmographic instrument is the pulse oximeter. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, through the patient's appendage. The transmitted signals are received by a detector that provides an analog electrical output signal representative of the received optical signals. By processing the electrical signal and analyzing signal values for each of the wavelengths at different portions of a patient's pulse cycle, information can be obtained regarding blood oxygen saturation.

The algorithms for determining blood oxygen saturation related values are normally implemented in a digital processing unit. Accordingly, one or more analog to digital (A/D) converters are generally interposed between the detector and the digital processing unit. Depending on the specific system architecture employed, a single multi-channel digital signal may be received by the digital processing unit or separate digital signals for each channel may be received. In the former case, the digital processing unit may be used to separate the received signal into separate channel components. Thus, in either case, the digital processing unit processes digital information representing each of the channels.

Such digital information defines input photoplethysmographic signals or "pleths." These pleths generally contain two components. The first component of interest is a low frequency or substantially invariant component in relation to the time increments considered for blood oxygen saturation calculations, sometimes termed the "DC component," which generally corresponds to the attenuation related to the non-pulsatile volume of the perfused tissue and other matter that affects the transmitted plethysmographic signal. The second component, sometimes termed the "AC component," generally corresponds to the change in attenuation due to the pulsation of the blood. In general, the AC component represents a varying waveform which corresponds in frequency to that of the heartbeat. In contrast, the DC component is a more steady baseline component, since the effective volume of the tissue under investigation varies little or at a low frequency if the variations caused by the pulsation of the heart are excluded from consideration.

Pulse oximeters typically provide as outputs blood oxygen saturation values and, sometimes, a heart rate and a graphical representation of a pulsatile waveform. The information for generating each of these outputs is generally obtained from the AC component of the pleth. In this regard, some pulse oximeters attempt to filter the DC component from the pleth, e.g., in order to provide a better digitized AC component waveform. Other pulse oximeters may measure and use the DC component, e.g., to normalize measured differential values obtained from the AC component or to provide measurements relevant to motion or other noise corrections. Generally, though, conventional pulse oximeters do not monitor variations in the DC component of a pleth or pleths to obtain physiological parameter information in addition to the outputs noted above. Although it has been proposed to use pulse oximeters to monitor other parameters including respiration rate, it is apparent that such proposed uses have not gained general commercial acceptance.

SUMMARY OF THE INVENTION

The present invention is directed to monitoring patient respiration based on a pleth signal. The invention thus provides important diagnostic or monitoring information noninvasively. Moreover, various aspects of the invention can be implemented using one or more channels and/or other components of a conventional pulse oximeter, thereby providing additional functionality to instruments that are widely available and trusted, as well as providing access to important information for treatment of patients on a cost-effective basis.

In accordance with one aspect of the present invention, a pleth signal is analyzed to identify a heart rate variability parameter associated with respiration rate. The associated process involves obtaining a pleth signal, processing the pleth signal to obtain heart rate samples, monitoring the heart rate samples to identify a heart rate variability, and determining a respiration rate based on the heart rate variability. It is known that heart rate varies with the respiration cycle, an effect called Respiratory Sinus Arrhythmia. The present invention provides a robust process for monitoring this effect and determining respiration rate based on pleth signals. A novel processor and pulse oximeter incorporating such processing are also provided in accordance with the present invention.

The step of obtaining a pleth signal generally involves receiving a digital signal representative of an optical signal modulated based on interaction with perfused tissue of a patient. Such a signal may be provided using components of a conventional pulse oximeter. Pulse oximeters typically transmit red and infrared signals, thereby yielding red and infrared pleths. Either or both of these pleths may be utilized in accordance with the present invention. In particular, each of these pleths generally has a fundamental frequency corresponding to the patient's heart rate. Accordingly, either pleth can be used to yield the desired heart rate information. In general, for normally oxygenated patients, the infrared channel typically has the stronger pleth waveform and may be preferred for heart rate calculations. For poorly oxygenated patients, the red pleth may be preferred. In many cases, a combination of the two signals may provide a better waveform for heart rate analysis than either signal alone.

The pleth may be processed to obtain heart rate samples in a variety of ways. As noted above, the pleth is generally a periodic signal having a fundamental frequency corresponding to the patient's heart rate. Accordingly, heart rate may be determined by performing peak-to-peak measurements on the pleth to determine the pulse period and, hence, pulse frequency. For example, such maxima may be obtained by identifying a change in sign of differential values between successive samples or groups of samples along the pleth or of a function fitted to the pleth. Alternatively, other points on the waveform, such as nominal zero (or average pleth value) crossings may be monitored. Such zero crossings would be expected to have a frequency of twice the heart rate. Such period measurements can be complicated due to the typically noisy waveform of the pleths. Accordingly, multiple waveforms may be utilized.

Additionally, the heart rate calculations may be performed in the frequency domain. In this regard, a processor may be configured to obtain a Fourier transform of the pleth. Once the Fourier transform is obtained, the pulse rate can be identified as the fundamental frequency of the pleth corresponding to the patient's heart rate. In any case, once the heart rate is determined, it can be monitored to identify low frequency variations associated with respiration. In particular, oscillatory variations having a frequency of between about 0.15 and 0.5 Hz and, especially, between about 0.2 and 0.4 Hz, are indicative of respiration rate. This range may be expanded to 0–5 Hz to accommodate the higher respiration rates of newborns.

One or more filters may be used in determining respiration rate information based on a pleth signal in accordance with the present invention. In this regard, an adaptive filter may be used to track the fundamental frequency of the pleth and, hence, the patient's pulse rate. For example, such a filter may function as a narrow band pass filter having a band pass that is centered on the fundamental frequency of the pleth. The transfer function of the filter may be varied, e.g., based on analysis of successive waveforms, to track the changing fundamental frequency. The filter or associated logic may thus be adapted to output a time series of pulse rate values. Such a time series of pulse rate values, whether obtained as an output of an adaptive filter system or otherwise, may be filtered using a static band pass filter having a pass band including the noted frequencies of interest, or using an adaptive filter that tracks a selected spectral peak of the time series to provide an output indicative of respiration rate. Such filtering provides a fast, robust and computationally efficient mechanism for noninvasively monitoring patient respiration based on pleth signals.

The present invention is based in part on a recognition that the pleth signal includes a variety of information in addition to the pulsatile waveform that is generally the focus of plethysmographic processing. In particular, it has been recognized that the pleth signal includes at least three additional or related components: 1) a component related to respiration or the "respiration wave", 2) a low frequency component associated with the autonomic nervous system or vaso motor center, sometimes termed the "Mayer wave," and 3) a very low frequency component which is associated with temperature control. Regarding the second of these, the origin and nature of the Mayer wave is not fully settled. For present purposes, the Mayer wave relates to a low frequency variation in blood pressure, heart rate, and/or vaso constriction.

The first two components noted above have particular significance for diagnostic and patient monitoring purposes. In particular, the amplitude and frequency of the Mayer wave are seen to change in connection with hypertension, sudden cardiac death, ventricular tachycardia, coronary artery disease, myocardial infarction, heart failure, diabetes, and autonomic neuropathy and after heart transplantation. Respiration rate is monitored during a variety of medical procedures, for example, as an indication of a patient's stress levels and to identify patient respiratory distress. It is expected that both the Mayer and respiration waves influence heart rate (and related parameters such as variations in blood pressure and blood volume) by direct influence on the vaso motor center. In the latter case, this is by a "spillover" from the breathing center to the vaso motor center, which increases heart rate during inspiration.

A difficulty associated with obtaining physiological parameter information based on the Mayer wave and the respiration wave relates to distinguishing the effects associated with these waves, particularly in view of the fact that each of these waves can occur within overlapping frequency ranges. In accordance with the present invention, respiration information is obtained by monitoring heart rate variability within a specific frequency band as noted above. In particular, by monitoring in a frequency range having a lower end of preferably at least about 0.15 Hz, for example, 0.15–0.5, interference due to Mayer wave effects can generally be minimized. Still better results may be obtained by monitoring a range between about 0.2–0.4 Hz or, especially, about 0.3 Hz. In the case of tracking respiration rate using an adaptive filter relative to a time series of pulse rate values or a corresponding frequency spectrum, the transfer function may be limited to track the respiration related peak only within these ranges using 0.3 Hz as an initial condition.

BRIEF DESCRIPTION OF THE DRAWINGS

For a more complete understanding of the present invention and further advantages thereof, reference is now made to the following detailed description, taken in conjunction with the drawings, in which.

DETAILED DESCRIPTION

The present invention relates to obtaining physiological parameter information for a patient based on an analysis of a pleth involving distinguishing an effect associated with a Mayer wave component from an effect associated with a respiration wave component. In the following discussion, the invention is described in the context of an implementation utilizing components of a conventional pulse oximeter. The invention has particular advantages in this regard as such an implementation enhances the functionality of conventional pulse oximeters and provides important physiological parameter information in a cost effective manner. However, it will be appreciated that various aspects of the invention are not limited to such a pulse oximeter or other multi-channel signal implementation and the invention may be embodied in a dedicated single or multi-channel photoplethysmography instrument. Accordingly, the following discussion should be understood as exemplifying the invention and not by way of limitation.

Figure 1:
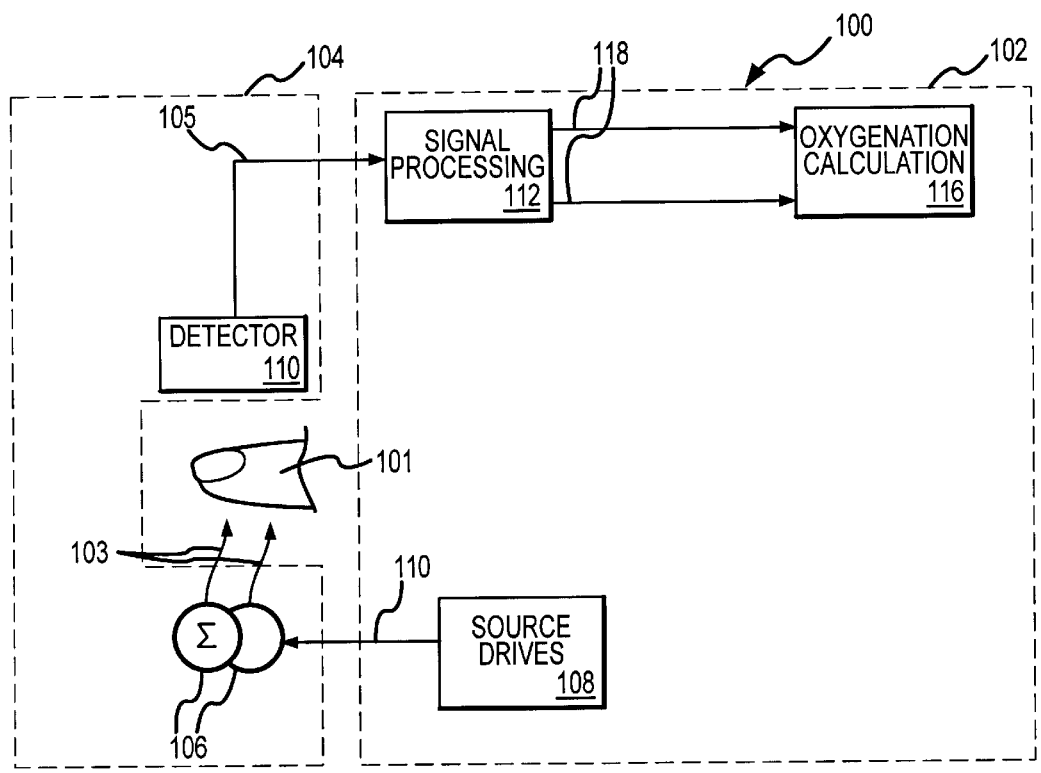
FIG. 1 is a schematic diagram of a pulse oximeter in accordance with the present invention.

Referring to FIG. 1, a schematic diagram of a pulse oximeter 100 in accordance with the present invention is shown. The oximeter 100 generally includes an instrument housing 102 and a probe 104 for attachment to a finger 101 or other appendage of a patient under analysis. In the illustrated embodiment, the probe 104 includes two or more sources 106 and a detector 110. It will be appreciated that either or both of these components may alternatively be located in the housing 102 and may be optically connected to the probe 104 by fiber optics or the like. Additionally, the sources 106 and/or detector 110 may be located in the cable or other coupling operatively between the probe 104 and the housing 102. The sources 106 are driven by source drives 108. The drives 108 serve to modulate the signals 103 in any of various ways. In this regard, the signals 103 transmitted by the sources 106 may be time division multiplexed, frequency division multiplexed, code division multiplexed, or the like. Such multiplexing facilitates separation of the signals from each of the channels during hardware or software based signal processing. The sources 106 provide two or more channels of signals 103. Each channel has a unique spectral content, e.g., wavelength or wavelength band. In the illustrated embodiment, two sources 106 are shown; one of the sources may have a red-centered wavelength and the other may have an infrared-centered wavelength.

The signals 103 may be transmitted through or reflected by the patient's tissue. In either case, the signals are modulated by the patient's tissue to provide information regarding blood oxygen saturation in a manner that is well known. The transmitted signals 103 are received by the detector 110 which, in the illustrated embodiment, provides an analog current output signal 105 representative of the detected signals 103. This detector signal 105 is then processed by signal processing module 112. The processing module 112 may include a number of components that may be embodied in software, firmware and/or hardware. These components may include components for amplifying the signal 105 and converting the signal from a current signal to a voltage signal, filtering the signal to remove certain components of noise and otherwise conditioning the signal. In the illustrated embodiment, the signal processing module 112 also includes an analog to digital converter for converting the signal into a digital signal and a demultiplexer component for providing two separate output signals 118 or pleths that generally correspond to the two separate channel signals 103. These pleths 118 are then used by oxygenation calculation module 116 to compute a value related to blood oxygen saturation, e.g., a blood oxygen saturation percentage. A number of algorithms for performing such calculations are known and such calculation techniques are disclosed in U.S. Pat. Nos. 5,934,277 by Mortz and 5,842,979 by Jarman, both of which are incorporated herein by reference.

Figure 2:
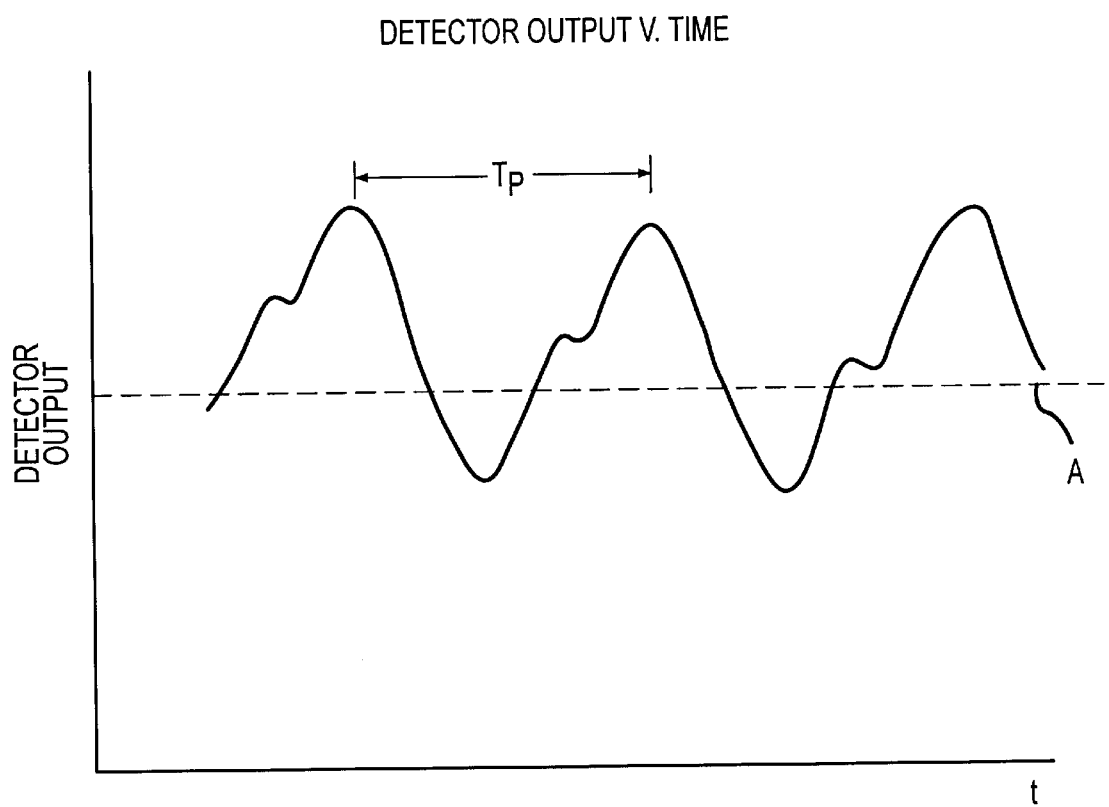
FIG. 2 illustrates the waveform of a pleth that may be used to obtain respiratory information in accordance with the present invention.

FIG. 2 illustrates an exemplary waveform of a pleth as such information may be obtained by the processor of a pulse oximeter. In particular, such information may be obtained as a digital signal output by the A/D converter, i.e., a time series of values related to the detector output. Such values are shown graphically in FIG. 2. As noted above, the pleth corresponding to either of the oximetry channels, or a combination of the channels, may be used in accordance with the present invention. It is desirable to obtain a strong pleth signal so that the waveform and pulse rate can be accurately identified. Accordingly, for normally oxygenated patients, the infrared channel pleth may be utilized. For poorly oxygenated patients, the red pleth may be preferred. In this regard, a cut off oxygenation level such as 85% may be used in determining whether to use the infrared or red pleth. Alternatively, the two pleth signals may be mathematically blended, depending on the current oxygenation level to obtain an optimized pleth for subsequent analysis in accordance with the present invention. Appropriate techniques for obtaining an optimized pleth signal are disclosed in U.S. patent application Ser. No. 09/975,289, which is disclosed herein by reference.

As shown in FIG. 2, the pleth signal includes a pulsatile component having a period designated $T_P$. This period corresponds to the patient's heart rate. The heart rate can be determined by monitoring this pleth in a variety of ways such as identifying a change in sign of a differential value of the waveform (e.g., to perform a peak-to-peak period measurement or peak-to-trough ½ period measurement), tracking crossings of an average value indicated by A, or, as will be discussed in more detail below, by using a filter to track the fundamental frequency of the pleth.

Figure 3:
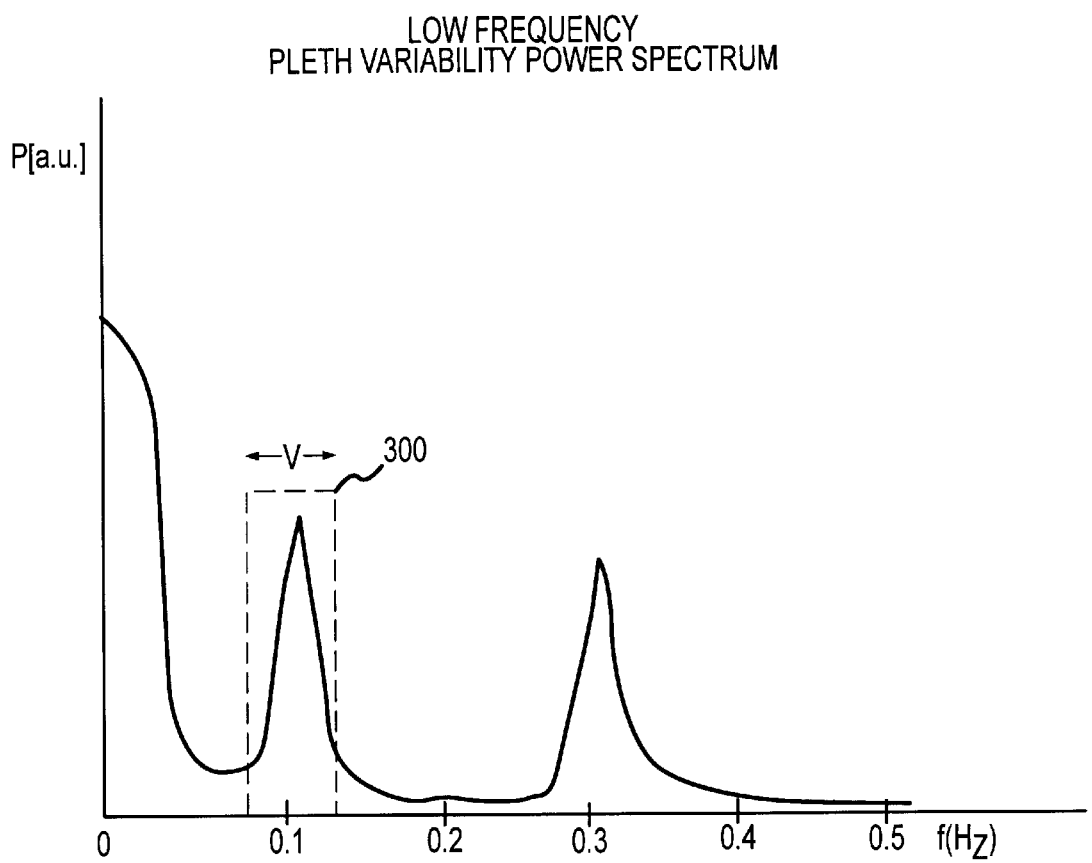
FIG. 3 illustrates a pleth power spectrum showing the respiration related peak that is used in accordance with the present invention.

In accordance with the present invention, the patient's respiration is monitored by tracking low frequency heart rate changes. FIG. 3 shows an exemplary pleth power spectrum. The spectrum is characterized by three discrete peaks. These include a peak typically around 0.3 Hz–0.5 Hz, a peak typically around 0.1 Hz and a peak below 0.05 Hz. The peak below 0.05 Hz is generally linked with vaso motor control and temperature control. The peak at around 0.1 Hz is generally associated with the Mayer wave. As noted above, this phenomenon is not well understood but has been correlated to hypertension, sudden cardiac death, ventricular tachycardia, coronary artery disease, myocardial infarction, heart failure, diabetes, and autonomic neuropathy and has been seen to change after heart transplantation. The remaining peak, at about 0.3–0.5 Hz is believed to be correlated with respiration and is of particular interest for purposes of the present invention. It will be appreciated that this peak may be as high as 1 Hz or greater for newborns.

Figure 4:
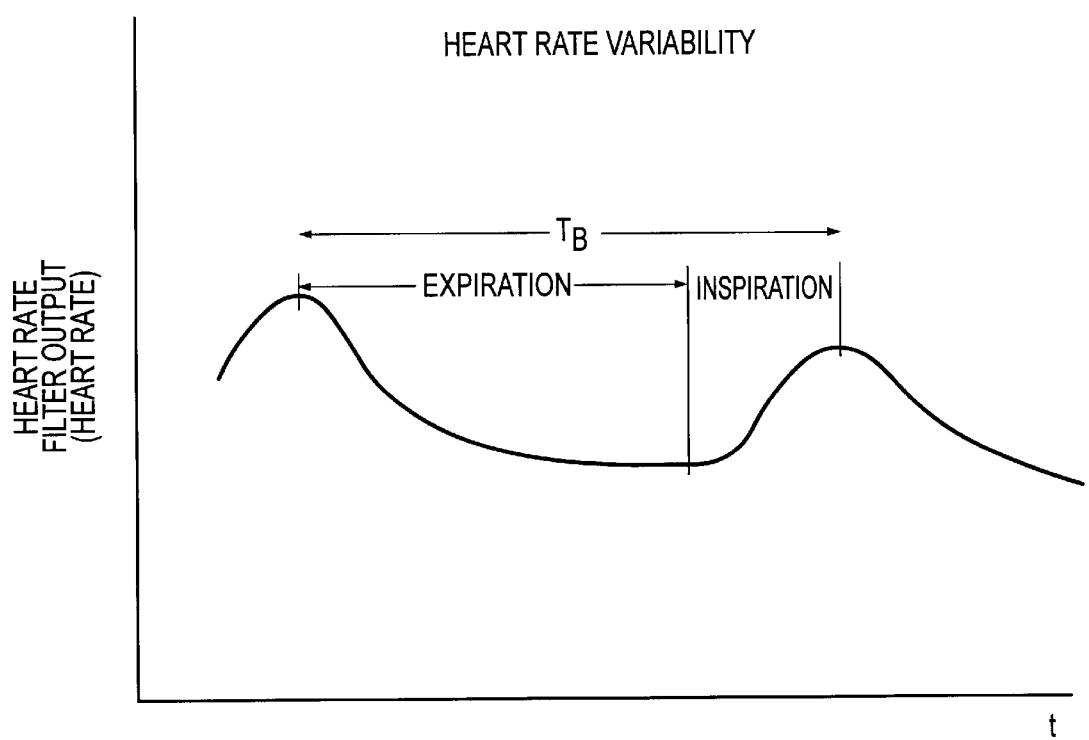
FIG. 4 illustrates a heart rate time series generated using an appropriate filter in accordance with the present invention.

FIG. 4 graphically illustrates the respiratory Sinus Arrhythmia phenomenon associated with the above noted respiration wave. In particular, FIG. 4 is a graph plotting the output of a heart rate filter, as will be discussed below, against time. As shown, the result is a periodic waveform having a period designated $T_B$. This generally corresponds to a reduction in heart rate during the expiration portion of the respiratory cycle and an increase in heart rate during the inspiration portion of the cycle. The period of this waveform generally corresponds to the respiration rate and is tracked using a pulse oximeter in accordance with the present invention.

From the foregoing discussion, it will be appreciated that respiration rate can be monitored by: 1) determining heart rate based on an analysis of the pleth signal, 2) monitoring this heart rate over time to obtain a time series heart rate values, and 3) analyzing the time series heart rate values to identify a respiration rate. These steps can be executed using adaptive filters and/or static band pass filters as discussed below.

Figure 5:
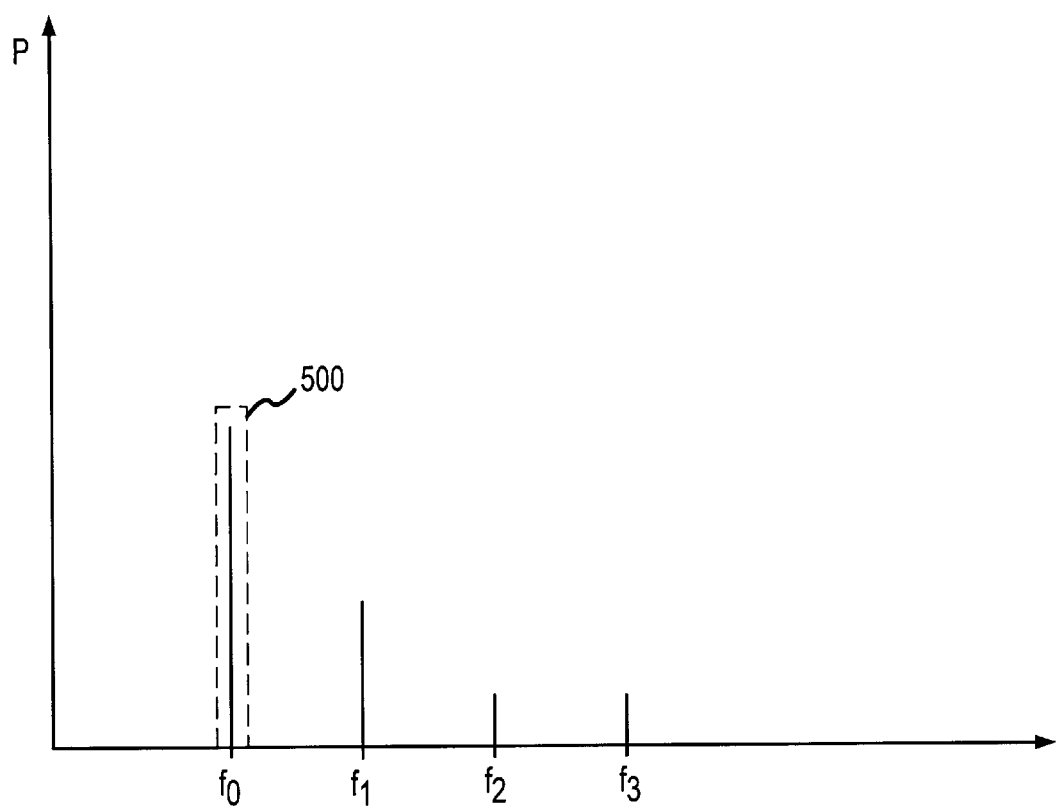
FIG. 5 is a pleth power spectrum illustrating a transfer function of a filter in accordance with the present invention.

FIG. 5 illustrates a pleth power spectrum. Such a power spectrum may be obtained by configuring the oximeter processor to mathematically obtain a Fourier transform of the time domain pleth signal. As shown, the pleth power spectrum has a fundamental frequency at $t_0$ corresponding to the patient's heart rate. Additional peaks of the illustrated power spectrum relate to harmonics thereof. The present invention utilizes an adaptive filter adapted to function as a band pass filter having a narrow band pass encompassing the fundamental frequency. The transfer function of this filter is generally indicated by function 500. A variety of different types of filters may be used in this regard. Generally, such filters track the fundamental frequency of a signal based on certain programmed information regarding the nature of the signal as well as by monitoring successive signal waveforms. Such filters are robust in operation and can provide a continually updated output, in this case, regarding pulse rate. Thus, such a filter can provide as an output a time series of pulse rate values such as illustrated in FIG. 4.

Figure 6:
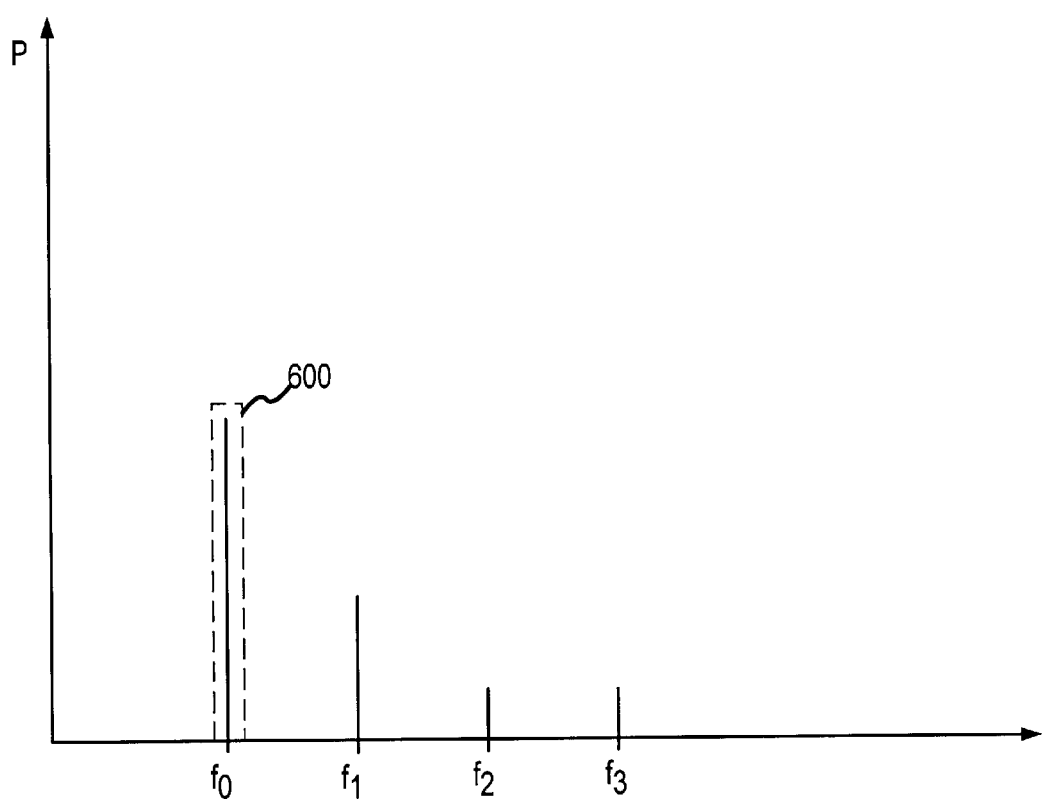
FIG. 6 is a respiratory power spectrum illustrating a transfer function of another filter in accordance with the present invention.

An additional digital filter can be used to track respiration rate. In particular, the output of the heart rate filter can be processed to provide a respiratory power spectrum as shown in FIG. 6. For example, the oximeter processor can be configured to perform a Fourier transform on the time series of pulse rate values output by the heart rate filter. The resulting respiratory power spectrum includes a frequency peak correlated to the respiration rate designated as $t_0$. The additional peaks shown in the power spectrum of FIG. 6 relate to harmonics thereof or other heart rate variations. An adaptive filter having a transfer function, generally indicated by function 600, can be used to track the fundamental frequency. Such a filter may be similar to the heart rate filter as described above and is programmed to adaptively track the noted frequency of the respiratory power spectrum which corresponds to respiration rate. The output of this filter is a periodically updated respiration rate value. Alternatively, a static band pass filter may be used to isolate the peak related to respiration and, hence, identify the respiration rate. Such a filter may have a pass band of 0–0.5 Hz or, to accommodate neonatal applications, 0–1.5 Hz.

Figure 7:
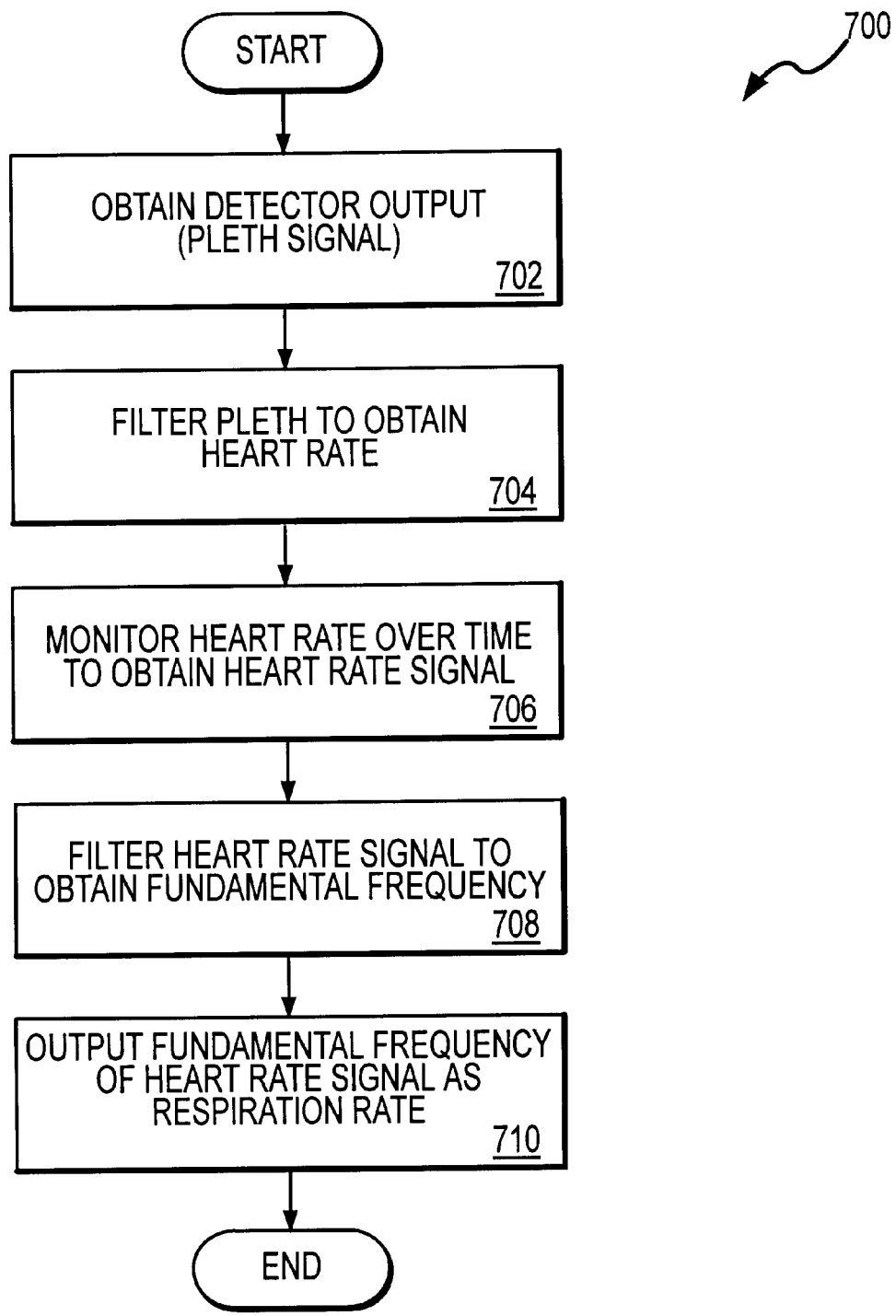
FIG. 7 is a flow chart illustrating a process for using a pleth signal to monitor respiration in accordance with the present invention.

FIG. 7 is a flow chart illustrating a process for determining respiration rate based on pleth signals in accordance with the present invention. The process 700 is initiated by obtaining a detector output or pleth signal. In the context of a pulse oximeter, this may involve receiving the digital output from an A/D converter that reflects the detector signal, demodulating this signal to obtain individual channel components and selecting a pleth for further processing. The selected pleth may be one of the channels or an optimized pleth based on both of the channel components. The pleth is then filtered (704) to obtain a time series of heart rate values. These values are monitored (706) over time to obtain a heart rate signal. The heart rate signal is then filtered (708) to identify a frequency peak correlated to respiration. The frequency of this peak is then output (710) as a respiration rate. This respiration rate may be displayed in the display area of a conventional pulse oximeter programmed to provide such information.

Figure 8:
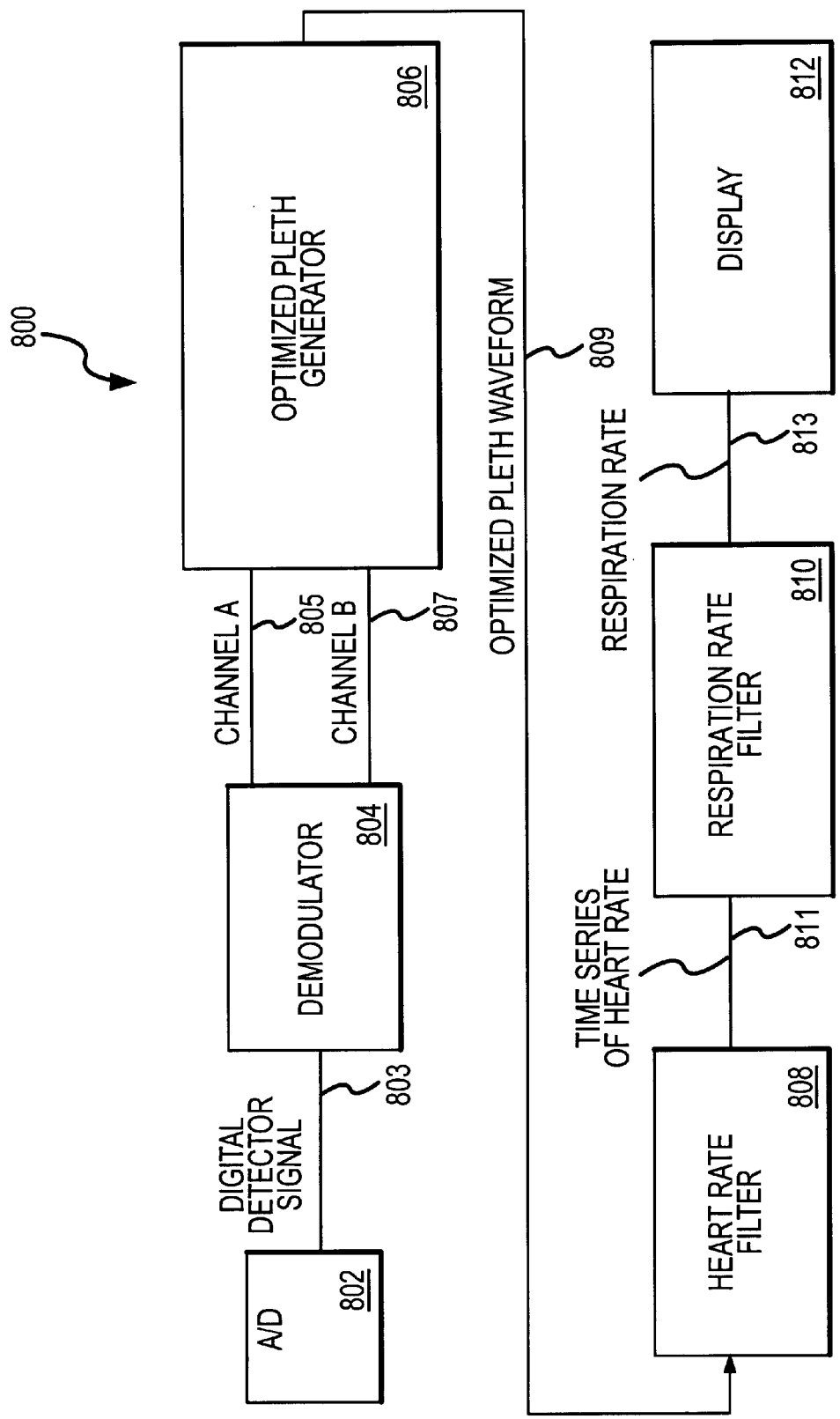
FIG. 8 illustrates a signal processing system in accordance with the present invention.

The corresponding components of a pulse oximeter processing unit are illustrated in FIG. 8. The illustrative unit 800 includes an A/D converter 802. The A/D converter receives an analog signal representative of the optical signal received by the pulse oximeter detector. This analog input signal is processed by the converter (802) to provide a digital detector signal 803. The digital detector signal 803 is then processed by demodulator 804 to provide two separate channel signals designated channel A (805) and channel B (807), that may correspond, for example, to the red and infrared channels of the pulse oximeter. These channel signals are then processed by the optimized pleth generator 806 to provide an optimized pleth waveform 809. As discussed above, the optimized pleth waveform may correspond to either of the channel signals or a combination thereof. This optimized waveform 809 is processed by a heart rate filter in order to track the fundamental frequency of the waveform which corresponds to the patient's heart rate. The output from the heart rate filter 808 is a time series of heart rate values 811. This time series heart rate values is then processed by a respiration rate filter 810 which tracks a selected frequency of the corresponding spectrum to determine respiration rate 813. The patient's respiration rate 813 may be periodically output to a user via a display 812.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed:

1. A method for use in monitoring a patient, comprising the steps of:
    obtaining a photoplethysmographic ("pleth") signal that is modulated based on interaction of a transmitted optical signal having at least two wavelength cannels with a patient's blood;
    first processing at least a first portion of said pleth signal to obtain a blood oxygen related value associated with said patient's blood;
    based on said blood oxygen related value, selecting at least one of said wavelength channels of said pleth signal for additional processing;
    second processing at least a second portion of said at least one wavelength channel of said pleth signal to obtain heart rate information regarding a heart rate of said patient; and
    third processing said heart rate information to obtain respiration information regarding respiration of said patient.

2. A method as set forth in claim 1, wherein said step of obtaining a pleth signal comprises operating a pulse oximeter to obtain a detector signal corresponding to at least two different wavelength channels of transmitted light.

3. A method as set forth in claim 2, wherein said step of selecting comprises selecting a signal component corresponding to one of said two channels as said pleth signal.

4. A method as set forth in claim 2, wherein said step of selecting comprises selecting signal components corresponding to both of said channels.

5. A method as set forth in claim 1, wherein said step of second processing comprises identifying characteristics of a waveform of said pleth signal corresponding to a pulse cycle of said patient so as to determine one of a period and a frequency of said pulse cycle.

6. A method as set forth in claim 1, wherein said step of second processing comprises performing a spectral analysis of said pleth signal to obtain said heart rate information.

7. A method as set forth in claim 1, wherein said step of second processing comprises using a filter to identify a spectral peak corresponding to said heart rate of the patient.

8. A method as set forth in claim 1, wherein said step of second processing comprises obtaining a heart rate signal reflecting a time series of heart rate values for said patient.

9. A method as set forth in claim 8, wherein said step of third processing comprises identifying a variation in said heart rate signal of said patient associated with said respiration.

10. A method as set forth in claim 1, wherein said step of third processing comprises filtering said heart rate information to identify a variation therein within a frequency range between about 0–1.5 Hz.

11. A method as set forth in claim 10, wherein said variation is within a frequency range between about 0.15 and 0.5 Hz.

12. A method as set forth in claim 10, wherein said variation is within a frequency range between about 0.2–0.4 Hz.

13. A method as set forth in claim 1, further comprising the step of providing an output indicative of a respiration rate of said patient.

14. A method for use in monitoring a patient, comprising the steps of:
   obtaining a time-based photoplethysmographic ("pleth") signal that is modulated based on interaction of a transmitted optical signal with a patient's blood;
   transforming a selected portion of said time-based pleth signal to into a frequency domain pleth signal;
   obtaining a heart rate signal, from said frequency domain pleth signal, reflecting a time series of heart rate values for said patient
   processing said heart rate signal using at least one filter to distinguish a signal component of interest having a frequency corresponding to a respiration rate of said patient from a potentially interfering signal component; and
   providing an output indicative of said respiration rate of said patient based on said signal component of interest.

15. A method as set forth in claim 14, wherein said filter is used to identify a spectral peak in said heart rate signal associated with said respiration rate of said patient.

16. A method as set forth in claim 14, wherein said filter is used to transform said heart rate signal to into a frequency domain respiration signal to identify said respiration rate from said heart rate signal.

17. An apparatus for use in monitoring a patient, comprising:
   a port for receiving a photoplethysmograph ("pleth") signal that is modulated based on interaction of a transmitted optical signal with a patient's blood; and
   a processor operative for:
   first processing said pleth signal to determine a blood oxygen level associated with said patient's blood;
   based on said blood oxygen level, second processing a selected portion said pleth signal to obtain heart rate information regarding a heart rate of said patient; and
   third processing said heart rate information to obtain respiration information regarding respiration of said patient.

18. An apparatus as set forth in claim 17, wherein said apparatus further comprises a source for transmitting an optical signal including at least one wavelength channel relative to a patient, a detector for receiving said transmitted optical signal and a signal processing module for processing a signal from said detector to provide said pleth signal.

19. An apparatus as set forth in claim 18, wherein said processor includes a module for identifying characteristics of a waveform of said pleth signal corresponding to a pulse cycle of said patient so as to determine one of a period and a frequency of said pulse cycle.

20. An apparatus as set forth in claim 17, wherein said processor is operative to perform a spectral analysis of said pleth signal to obtain said heart rate information.

21. An apparatus as set forth in claim 17, wherein said processor includes a filter for identifying a spectral peak corresponding to said heart rate of said patient.

22. An apparatus as set forth in claim 17, wherein said processor is operative for identifying a variation in said heart rate of said patient associated with said respiration.

23. The method of claim 3, wherein said two channels comprise a red channel and an infrared channel, wherein said step of selecting comprises selecting the red channel if said blood oxygen value is less than about 85%.

24. A method as set forth in claim 14, wherein said step of obtaining a pleth signal comprises operating a pulse oximeter to obtain a detector signal corresponding to at least two different wavelength channels of transmitted light.

25. A method as set forth in claim 24, wherein one of said two different channels is selected for said second processing if said blood oxygen level is within a a predetermined range.

26. A method for use in monitoring a patient, comprising the steps of:
   obtaining a photoplethysmographic ("pleth") signal that is modulated based on interaction of a transmitted optical signal with a patient's blood, said pleth signal being in the time domain;
   first performing a transform on said time domain pleth signal to obtain spectral information, said spectral information being in the frequency domain;
   second performing a transform based on said spectral information to obtain transformed information; and
   identifying a physiological parameter of interest based on said transformed information.

27. The method of claim 26, wherein said step of obtaining comprises obtaining a pleth signal having at least two wavelength channels.

28. the method of claim 27, further comprising:
   processing said pleth signal to obtain a blood oxygen value associated with said patient's blood; and
   based on said blood oxygen level, selecting at least one of said wavelength channels of said pleth signal for additional processing.

29. The method of claim 26, further comprising;
   prior to said second performing step processing said spectral information to obtain a power pleth spectrum signal.

30. The method of claim 29, wherein said step of processing comprises identifying a spectral peak associated with a heart rate of said patient.

31. The method of claim 30, wherein said step of identifying further comprises generating a time series of heart rate values for said patient.

32. The method of claim 31, wherein said second performing step comprise transforming said time series of heart rate values to obtain respiratory information, said respiratory information being in the frequency domain.

33. The method of claim 32, wherein a spectral peak of said respiratory information in said frequency domain is associated with respiration.

34. A method for use in monitoring a patient, comprising the steps of:

obtaining a time-based photoplethysmographic ("pleth") signal that is modulated based on interaction of a transmitted optical signal having at least two wavelength channels with a patient's blood;

first processing an AC component of at least one of said wavelength channels to obtain a heart rate signal reflecting a time series of heart rate values for said patient;

second processing said heart rate information to obtain respiration information regarding respiration of said patient.

35. The method of claim 34, further comprising:

processing at least a first portion of said pleth signal to obtain a blood oxygen related value associated with said patient's blood;

and based on said blood oxygen related value, selecting at least one of said wavelength channels of said pleth signal for said first processing step.

36. The method of claim 34, wherein said first processing step includes:

transforming said time-based pleth signal into spectral information;

identifying a spectral peak associated with a heart rate of said patient; and using a plurality of temporally distinct spectral peaks associated with said heart rate to generate said heart rate signal, wherein said heart rate signal is a time-based signal.

37. The method of claim 34, wherein said second processing step comprises transforming said heart rate signal into a frequency-based signal.

38. The method of claim 37, further comprising identifying a spectral peak in said frequency-based signal associated with a respiration rate of said patient.

* * * * *